US012398019B2

(12) United States Patent
Häberle et al.

(10) Patent No.: US 12,398,019 B2
(45) Date of Patent: Aug. 26, 2025

(54) PASSENGER TRANSPORT SYSTEM WITH DISINFECTION DEVICE AND METHOD FOR OPERATING SAME

(71) Applicant: INVENTIO AG, Hergiswil (CH)

(72) Inventors: Ulrich Häberle, Purkersdorf (AT); Gerhard Kleewein, Pressbaum (AT); Georg Wagenleitner, Roßleithen (AT)

(73) Assignee: Inventio AG, Hergiswil (CH)

( * ) Notice: Subject to any disclaimer, the term of this patent is extended or adjusted under 35 U.S.C. 154(b) by 206 days.

(21) Appl. No.: 18/005,474

(22) PCT Filed: Jun. 17, 2021

(86) PCT No.: PCT/EP2021/066516
§ 371 (c)(1),
(2) Date: Jan. 13, 2023

(87) PCT Pub. No.: WO2022/012855
PCT Pub. Date: Jan. 20, 2022

(65) Prior Publication Data
US 2023/0271811 A1 Aug. 31, 2023

(30) Foreign Application Priority Data
Jul. 17, 2020 (EP) .................................. 20186511

(51) Int. Cl.
*B66B 31/00* (2006.01)
*A61L 2/10* (2006.01)
(Continued)

(52) U.S. Cl.
CPC ............. *B66B 31/006* (2013.01); *A61L 2/10* (2013.01); *A61L 2/24* (2013.01); *B66B 25/003* (2013.01); *A61L 2202/14* (2013.01)

(58) Field of Classification Search
CPC ... B66B 31/006; B66B 25/003; B66B 25/006; B66B 31/02; A61L 2/10; A61L 2/24; A61L 2202/14
See application file for complete search history.

(56) References Cited

U.S. PATENT DOCUMENTS 9,833,527 B1 * 12/2017 Ting .................. B66B 31/02
2021/0279981 A1 * 9/2021 Mustonen .............. G07C 5/008

FOREIGN PATENT DOCUMENTS

| CN | 102556826 A | * | 7/2012 | ............. A61L 2/202 |
| CN | 106608587 A | * | 5/2017 | |

(Continued)

OTHER PUBLICATIONS

IPSearch History May 23, 2025 UTC; InnovationQ+; https://iq.ip.com/discover (Year: 2025).*

(Continued)

*Primary Examiner* — Gene O Crawford
*Assistant Examiner* — Abby A Jorgensen
(74) *Attorney, Agent, or Firm* — Knobbe, Martens, Olson & Bear, LLP

(57) ABSTRACT

A passenger transport system and a method of operating the same are described. The passenger transport system includes a passenger conveying device, a control unit for controlling an operation of the passenger conveying device, and a disinfecting device for disinfecting a surface to be disinfected on the passenger conveying device. The disinfecting device includes a controller for controlling an operation of the disinfecting device. The control unit of the passenger transport system and the controller of the disinfection device are adapted in such a manner that status signals, which reflect information about a current operation, a current state, and/or a current configuration of the disinfection device, are sent from the controller to the control unit, and the control unit generates control signals taking into account received (Continued)

status signals and transmits them to the controller, wherein the controller controls the operation of the disinfection device taking into account received control signals.

14 Claims, 1 Drawing Sheet

(51) Int. Cl.
    *A61L 2/24*          (2006.01)
    *B66B 25/00*       (2006.01)

(56) References Cited

FOREIGN PATENT DOCUMENTS

| | | | | | |
|---|---|---|---|---|---|
| CN | 111346247 | A | * | 6/2020 | ............... A61L 2/22 |
| DE | 102020114252 | A1 | * | 10/2021 | |
| JP | 2012082051 | A | * | 4/2012 | ............. A61L 2/202 |
| JP | 20120037900 | A | | 4/2012 | |
| JP | 2017220328 | A | | 12/2017 | |
| KR | 20120037900 | A | * | 4/2012 | |
| TW | 201233618 | A | | 8/2012 | |
| WO | WO-2019059858 | A2 | * | 3/2019 | ............. B66B 31/02 |

OTHER PUBLICATIONS

International Search Report for International Application No. PCT/EP2021/066516 dated Nov. 3, 2021.

\* cited by examiner

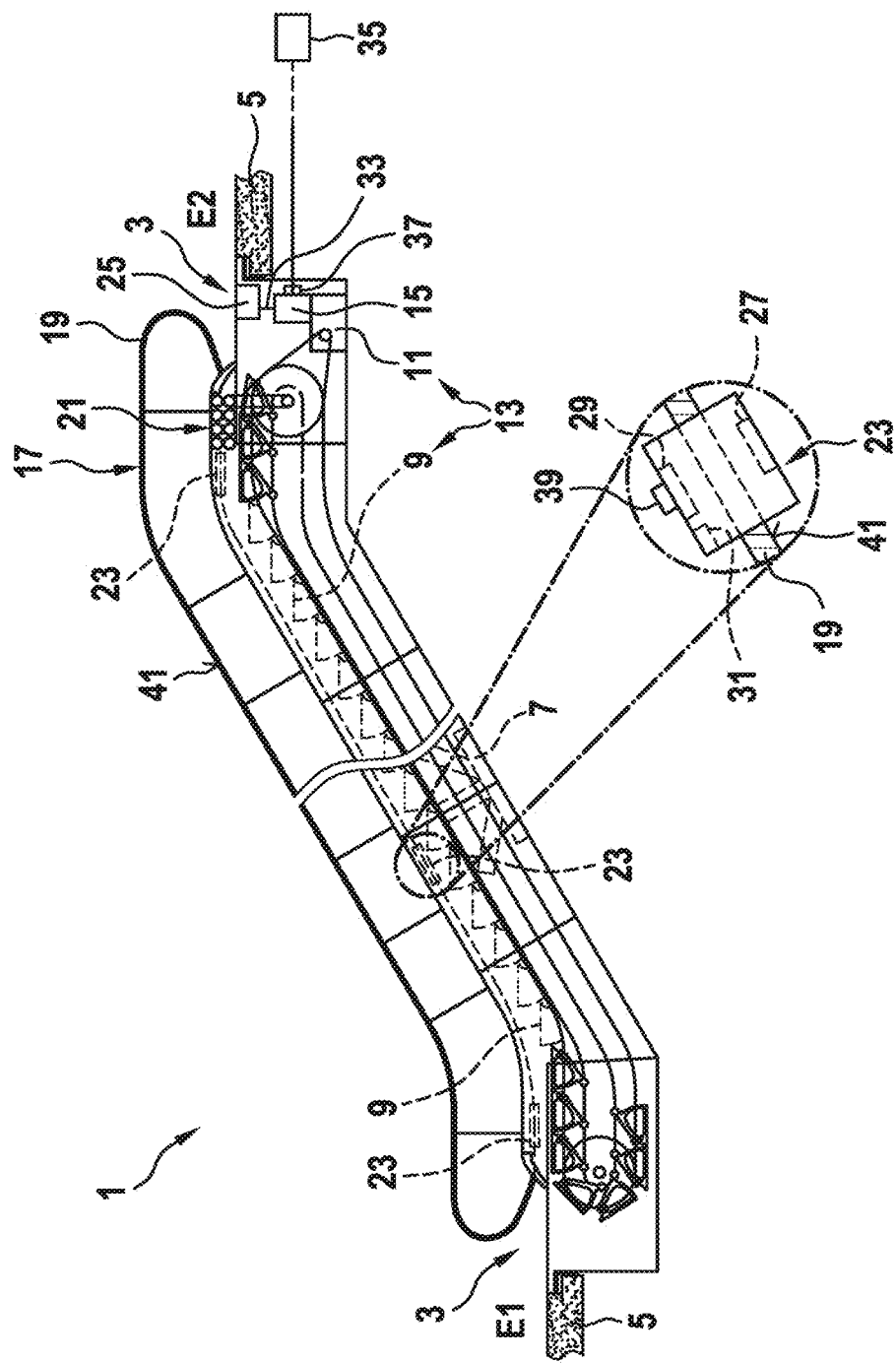

PASSENGER TRANSPORT SYSTEM WITH DISINFECTION DEVICE AND METHOD FOR OPERATING SAME

TECHNICAL FIELD

The present disclosure relates to a passenger transport system, in particular, to a passenger transport system which has a disinfection device, and to a method for operating such a passenger transport system.

SUMMARY

Passenger transport systems are used to transport people within buildings or structures. Passenger transport systems can be configured in the form of escalators, moving walkways or elevators, for example.

Germs in the form of viruses, bacteria and/or microbes can accumulate on the surfaces of a passenger transport system. To prevent their transmission to passengers of the passenger transport system, a disinfection device can be provided in the passenger transport system. The disinfection device can be designed to disinfect the relevant surfaces, for example, by killing and/or removing germs located thereon.

One possible design of a disinfection device utilizes light sources, such as light-emitting diodes (LEDs), which emit germicidal electromagnetic radiation. For example, so-called UVC LEDs can be used for this purpose, which emit high-energy ultraviolet radiation, which is also referred to as UVC radiation and typically has a wavelength range of 100-25 300 nm, usually 180-260 nm.

The earlier Patent Application EP20165562.8, filed at an earlier date by the applicant of the present patent application, describes a passenger transport system in the form of an escalator or moving walkway, which is equipped with a disinfection device in the form of a handrail disinfection device. The handrail disinfection device preferably uses UVC LEDs to irradiate and thus disinfect a handrail from different directions. Similar embodiments as described for the handrail disinfection device in the earlier patent application can also be implemented for the disinfection device of the passenger transport system described in the present patent application. The contents of the earlier patent application are intended to be incorporated herein by reference in their entirety.

Furthermore, in JP 2017 220328 A, a device for estimating a service life of an LED is described. CN 106 608 587 A discloses a passenger transport system with a disinfection device and sensors integrated in the handrail. A control unit of the passenger transport system is connected to the sensors and the disinfection device via a communication module.

There may be a need for a passenger transport system and a method for operating same, which make it possible to reliably operate the passenger transport system with little effort and, in particular, to disinfect surfaces on the passenger transport system reliably and with low maintenance requirements and at low cost.

Such a need can be met by the subject matter according to any of the independent claims. Advantageous embodiments are defined in the dependent claims as well as in the following description.

According to a first aspect of the disclosure, a passenger transport system is proposed which comprises a passenger conveying device for conveying passengers within a building structure, a control unit for controlling an operation of the passenger conveying device, and a disinfecting device for disinfecting a surface to be disinfected on the passenger conveying device. The disinfection device has a controller for controlling an operation of the disinfection device. The controller of the disinfecting device is connected to the control unit of the passenger conveying device via a bidirectional communication system. The control unit of the passenger transport system and the controller of the disinfection device are configured in such a manner that status signals reflecting information about a current operation, a current state and/or a current configuration of the disinfection device are transmitted from the controller to the control unit, and the control unit generates control signals taking into account received status signals and transmits them to the controller, wherein the controller controls the operation of the disinfection device taking into account received control signals. Furthermore, the controller of the disinfection device is configured to control a disinfection intensity with which the disinfection device disinfects the surface to be disinfected, depending on control signals which are sent to the controller by the control unit of the passenger transport system. These control signals indicate here an operating parameter of the disinfection device that correlates with a current disinfection intensity to be achieved.

According to a second aspect of the disclosure, a method for operating a passenger transport system according to an embodiment of the first aspect is described. The method comprises at least the following steps:
transmitting status signals reflecting information about a current operation, a current state and/or a current configuration of the disinfection device from the controller to the control unit, and
controlling an operation of the disinfection device taking into account received control signals, which are transmitted from the control unit to the controller taking into account received status signals.

The status signals can optionally be sent from the control unit to a remotely arranged computer and processed there. Further, control signals may optionally be transmitted from the remotely arranged computer to the control unit and from the control unit further to the controller to control the operation of the disinfection device.

Possible features and advantages of embodiments of the disclosure may be considered, among other things and without limiting the disclosure, as based on ideas and findings described below.

Briefly summarized, an essential idea underlying the disclosure is that it has been recognized that a disinfection device in a passenger transport system should advantageously not be operated completely independently of other components of the passenger transport system. On the one hand, the way in which the disinfection device is currently to be operated may depend on conditions prevailing in other components of the passenger transport system and/or on operating conditions of the passenger transport system. On the other hand, conditions and states applicable to the disinfection device may also have a feedback effect on other components of the passenger transport system. Therefore, it is proposed to couple the controller of the disinfection device and the control unit of the passenger conveying device by means of a bidirectional communication system, so that signals and data can be transmitted between them in both directions. Thus, on the one hand, status signals indicating information concerning the disinfecting device and in particular concerning its current operation, current state and/or current configuration can be transmitted from the controller of the disinfecting device to the control unit of the passenger conveying device via the bidirectional communication system, so that this information can be taken into account when controlling the passenger conveying device and/or, if necessary, this information can be processed by the control unit and/or transmitted to other components, in particular to an external computer, for further processing there. On the other hand, control signals can be generated by the control unit of the passenger conveying device and transmitted to the controller of the disinfection device so that the latter can then be controlled in accordance with these control signals. In doing so, the control unit can take into account status signals previously received from the controller of the disinfection device when generating the control signals. Ultimately, the disinfecting device can therefore be controlled or regulated, for example, in a manner in which information to the control unit of the passenger conveying device as a result of its communication with other components of the passenger transport system as well as information relating to the disinfecting device itself is made available. The information can be used, for example, to detect at an early stage when components of the disinfection system are approaching the end of their service life, so that maintenance or replacement measures can be planned and initiated in good time. Furthermore, the information can also be used, for example, to be able to better assess the influences of the operation of the disinfection device on other components of the passenger transport system, for example, by taking the status signals relating to the disinfection device into account in the maintenance and analysis of a digital twin of the passenger transport system.

Possible features and advantages of embodiments of the passenger transport system and the operating methods thereof, respectively, are explained in more detail below.

The passenger transport system described can be designed as an escalator, moving walkway or elevator. The passenger conveying device of the passenger transport system is designed by means of a combination of a unit moving along a travel path and a drive to convey one or preferably more persons within the building structure. In the case of a design as an escalator, the passenger conveyor system has a step belt for this purpose, in which a number of steps are coupled to one another one behind the other in a direction of travel and which can be driven by a drive in a circulating manner. Similarly, the passenger conveying device of a moving walkway has a pallet belt with a plurality of pallets arranged one behind the other and coupled to each other, wherein the pallet belt can also be driven by a drive in a circulating manner. In the case of a design as an elevator, the passenger conveyor device has at least one elevator car, which typically can be moved vertically by a drive device within an elevator shaft.

The control unit of the passenger transport system is adapted to control the operation of the passenger conveying device and in particular the drive thereof. Among other things, a travel activity, a travel direction and/or a travel speed can be controlled in this connection. In doing so, various parameters and/or conditions can be taken into account. For example, in the case of an escalator or moving walkway, suitable sensors can be used to detect whether one or more people are present in an access area and/or on the step belt or pallet belt. Based on signals from such sensors, a control unit can then control the drive of the escalator or moving walkway to move the passengers in a desired direction and at a desired speed using the passenger conveying device. In the case of an elevator, for example, sensors, buttons or the like on control panels can be actuated by passengers to communicate to the control unit where the elevator car should be moved by the drive. When controlling the passenger conveying device, the control unit can take additional information into account. This can come from further sensors which, for example, determine ambient conditions or load conditions. The information can also come from other sources. For example, information or instructions contained therein can be transmitted to the control unit from external devices, such as a remotely arranged computer, to instruct the control unit how the passenger conveying device should currently be operated or controlled.

The disinfection device is adapted to disinfect at least one surface in the area of the passenger conveying device. In particular, the disinfection device should be able to disinfect surfaces that are frequently touched by passengers and can therefore promote the spread of germs between different passengers. For example, the disinfection device can disinfect a surface of a handrail of an escalator or moving walkway. In an elevator, for example, the disinfection device can disinfect surfaces on a control panel and/or grab handles or, if necessary, even the entire interior of an elevator car.

In a preferred design, the disinfection device here has a light source that can emit high-energy ultraviolet light to render germs harmless. For example, one or more UVC LEDs can serve as the light source. The disinfection intensity with which such a disinfection device disinfects surfaces depends to a large extent on an irradiation dose, that is, on how large the quantity of light is that strikes a given surface per unit of time. To ensure a sufficient disinfection effect, this irradiation dose or disinfection intensity should be greater than a minimum disinfection intensity to be determined in advance.

In general, however, the disinfection device can also be designed differently. For example, a surface to be disinfected can be sprayed or wetted by the disinfection device with a disinfecting liquid having a disinfecting effect, such as an alcohol. In this regard, a disinfection intensity may depend on a quantity, a temperature, a chemical composition, and/or other parameters of the applied disinfection liquid. Alternatively, a surface to be disinfected may be gassed by the disinfection device with a disinfecting gas having a disinfecting effect, such as ozone. In this case, a disinfection intensity may depend on a gas flow, a gas concentration, a gas temperature, a chemical composition of the gas and/or other parameters.

The disinfection device has a controller that controls the operation thereof. In particular, a disinfection activity, disinfection intensity and/or disinfection type can be controlled. The disinfection activity indicates here whether the disinfection device is currently activated or deactivated. The disinfection intensity specifies a measure of the disinfection effect to be achieved. The disinfection type can specify, for example, which action mechanism is currently to be used by the disinfection device.

The controller of the disinfection device can preferably control operating parameters which correlate with the disinfection activity to be effected by the disinfection device.

For example, the controller of a disinfection device that uses light sources to emit UV light as a disinfecting mechanism of action and the disinfection intensity of which depends predominantly on the light intensity can control the current supplied to the light sources as an operating parameter. The stronger this current, the higher the light intensity and typically the higher the disinfection intensity.

In principle, it would be conceivable for the disinfection device to be operated completely autonomously and independently of other components of the passenger transport system.

However, on the one hand, it has been recognized to be of advantage to be able to operate the disinfection device adapted to different operating conditions of the passenger transport system and thus as required.

For example, according to one embodiment, it may be advantageous if the control unit generates the control signals taking into account information about a speed at which the passenger conveying device is operated and/or a number of passengers conveyed by the passenger conveying device. In general, it can be assumed that a high number of persons to be transported may require an increased activity of the disinfection device. It can also be assumed that at higher speeds of the passenger conveying device, the disinfection device should be operated at a higher output than at lower speeds since, on the one hand, more passengers are presumably transported per unit time. On the other hand, it can be assumed that in the event that the surface to be disinfected is moved along with the passenger conveying device, as is the case, for example, with a handrail of an escalator, a duration within which this surface is disinfected by the disinfection device becomes shorter with increasing speed, so that disinfection should be carried out more quickly. In the case of an elevator system, it is again necessary to ensure that no person is in the elevator car during the disinfection process since the disinfecting measures usually involve biocidal products and thus could endanger the health of the users. Overall, due to the fact that information available, for example, to the control unit of the passenger transport system can also be used when controlling the disinfection device to enable a more demand-oriented operation of the disinfection device.

On the other hand, it has also been found to be advantageous to make information about a current status of the disinfection device accessible to other components of the passenger transport system and/or to provide such information to an external monitoring system of the passenger transport system.

For this purpose, it is proposed to couple the controller of the disinfection device and the control unit of the passenger conveying device via a bidirectional communication system. Such a bidirectional communication system allows data transmission in both opposite directions, e.g., from the control unit to the controller and from the controller to the control unit. The bidirectional communication system can be technically implemented in various ways, for example, by means of a bus system, Bluetooth communication or the like. It can be implemented in a wired or wireless manner.

In addition, both the controller of the disinfection device and the control unit of the passenger conveying device are each to be adapted to generate signals for their part and to transmit them to the respective other component as well as to receive signals from the other component.

Specifically, the controller of the disinfection device shall be able to generate status signals that reflect information about a current operation, a current state, and/or a current configuration of the disinfection device. For example, the information about the current operation indicates whether the disinfection device is currently active or deactivated. The information about the current state can indicate, for example, which target properties the disinfection device or its components have and/or which actual properties have emerged over time, for example, due to wear that has occurred and is preferably recorded. The current state can be determined, for example, by means of sensors and/or by analyzing previous states and taking into account past and current operating parameters and/or operating durations. For example, the information on the current configuration can indicate which of a plurality of possible parameter settings is currently being used to operate the disinfection device. In the case of a disinfection device operated with light sources, for example, the current configuration may include information about a current intensity supplied to the light sources.

The control unit of the passenger transport system shall be able to generate control signals itself and/or receive them from other sources, such as a remotely arranged computer, and then transmit them to the controller of the disinfection device. These control signals are intended to instruct the controller with which operating parameters the disinfection device is to be operated. In this context, the control signals may, for example, specify target requirements for a current operation and/or a current configuration of the disinfection device.

Due to the bidirectional communication and exchange of information between the disinfection device and the control unit of the passenger transport system, a current status of the disinfection device can thus be communicated to the control unit and taken into account by the control unit when controlling the disinfection device and/or other components of the passenger transport system. The information about the status of the disinfection device can be taken into account quasi in real time, so that a kind of feedback control of the disinfection device can be effected. Alternatively, the information can be accumulated over time, so that when controlling the disinfection device, its history can be taken into account, such as a duration of a previous operation, operating parameters set at that time (e.g., current supplied), environmental conditions prevailing at that time (e.g., temperatures), periods of use, etc. This can enable efficient, reliable and/or on-demand operation of the disinfection device.

As already mentioned above, the controller of the disinfection device is adapted to control a disinfection intensity with which the disinfection device disinfects the surface to be disinfected, depending on control signals which are transmitted to the controller by the control unit of the passenger transport system and which indicate an operating parameter of the disinfection device correlating with a disinfection intensity to be currently effected.

In other words, the bidirectional communication capability between the control unit of the passenger transport system and the controller of the disinfection device described above is to be used to control the operation of the disinfection device with regard to a disinfection intensity to be effected by means of control signals transmitted from the control unit of the passenger transport system to the controller of the disinfection device. The control signals instruct the controller of the disinfection device to set one or more operating parameters of the disinfection device in such a manner that the result is a desired disinfection intensity.

The disinfection intensity can be defined, for example, as a measure that specifies what percentage of a germ load present on a surface are to be rendered harmless within a unit of time.

For example, in a disinfection system with UV light sources, a control signal can indicate the electrical power to be supplied to the UV light sources. In doing so, the electrical power correlates with the light intensity emitted by the light sources over time and thus ultimately with the disinfection intensity effected.

According to a specific embodiment, the control unit can in particular generate control signals indicating a setpoint value for the operating parameter of the disinfection device correlating with a current disinfection intensity to be effected, taking into account the status signals received from the controller.

In other words, when generating the control signals, the control unit shall take into account the status signals currently received or received in a previous time period from the controller of the disinfection device. Accordingly, the disinfection device may be controlled in a manner in which, among other things, information about its own operation, status and/or configuration may be taken into account. In this regard, the control signals can indicate a setpoint value for the operating parameter that correlates with the disinfection intensity currently to be effected.

According to one embodiment, the disinfection device may be adapted to be able, in a new state, to effect as a maximum disinfection intensity a disinfection intensity which is greater than a minimum disinfection intensity necessary for sufficient disinfection of the surface to be disinfected. For this purpose, the control unit of the passenger transport system and/or the controller of the disinfection device can be adapted to operate the disinfection device in normal operation with a disinfection intensity above the minimum disinfection intensity and to successively increase an operating parameter of the disinfection device correlating with a currently effected disinfection intensity.

In other words, the disinfection device can be overdimensioned to a certain extent, e.g., designed in such a manner that it can achieve a maximum disinfection intensity that is higher than a minimum disinfection intensity that is at least necessary to sufficiently disinfect a germ-covered surface before signs of wear occur. The minimum disinfection intensity can be defined here in accordance with hygienic specifications. The overdimensioned maximum disinfection intensity can, for example, be higher than the minimum disinfection intensity by a predetermined percentage, for example, at least 10% or at least 20%.

It has been recognized that the disinfection intensity actually effected by the disinfection device may decrease over time due to wear and tear. For example, it was observed that a radiation intensity emitted by a UVC LED can decrease over time despite a constant supply current. Accordingly, previous disinfection devices were also always overdimensioned to a certain degree. Typically, such disinfection devices were always operated at their specified rated power, e.g., they were driven to deliver their maximum disinfection intensity. Initially, this resulted in a higher disinfection intensity than was necessary for reliable disinfection. This resulted in both increased energy consumption and increased wear on the disinfection device.

It is now proposed to use the initial overdimensioning of the disinfection device in such a way that, at the beginning of an operation, the disinfection device is operated with operating parameters that effect a disinfection intensity below the maximum disinfection intensity. Thus, the disinfection device should initially be operated with less than its rated power. However, the disinfection device should always be operated in such a way that an effected disinfection intensity is above the necessary minimum disinfection intensity.

In the course of time, the operating parameter of the disinfection device, which correlates with the currently effected disinfection intensity, is to be successively increased. By successively increasing the operating parameter, effects that reduce a disinfection intensity over time, for example, due to wear occurring in the disinfection device, can be compensated.

Overall, it can be achieved in this way that, on the one hand, a sufficient disinfection effect can always be guaranteed and, on the other hand, that the disinfection device is not operated with an excessively high disinfection intensity, so that energy consumption and wear can be minimized.

According to a specific embodiment, the control unit of the passenger transport system and/or the controller of the disinfection device can be adapted to increase the operating parameter of the disinfection device correlating with a currently effected disinfection intensity depending on an operating time since start-up of the disinfection device.

In other words, the operating parameter with which the disinfection device is operated and which correlates with the disinfection intensity effected can initially be operated with less than a rated power value and then successively increased depending on the operating time that has elapsed since the start-up of the disinfection device. The operating parameter can be increased at certain time intervals of, for example, several days or weeks, e.g., periodically, for example. Alternatively, the operating parameter can be increased linearly over time. Such an increase of the operating parameter, which depends only on the previous operating duration, can be simple and inexpensive to implement.

Depending on the extent of the initial overdimensioning of the disinfection device, it can be known how often or over what period of time the operating parameter can be increased until the disinfection device is finally operated at maximum permissible operating parameters and is thus close to the end of its service life.

According to a preferred embodiment, the disinfection device can further comprise a sensor for detecting a measured variable that correlates with the disinfection intensity. The control unit of the passenger transport system and/or the controller of the disinfection device can be adapted in this case to increase the operating parameter of the disinfection device correlating with a currently effected disinfection intensity depending on the measured variable detected by the sensor.

In other words, the disinfection device can preferably have a sensor by means of which the disinfection intensity actually effected by the disinfection device can be determined. The disinfection intensity actually effected by the disinfection device thus no longer needs to be estimated on the basis of the operating parameters with which the disinfection device is operated but can actually be measured by means of the sensor. A measured variable detected by this sensor can then be taken into account by the control unit or controller in order to be able to suitably adjust the operating parameter correlating with the disinfection intensity effected and to be able to increase it over time in such a manner that a sufficient, but not unnecessarily high disinfection intensity is always effected.

According to a further specific embodiment, the control unit of the passenger transport system and/or the controller of the disinfection device can be adapted to regulate the operating parameter of the disinfection device correlating with a currently effected disinfection intensity depending on the measured variable detected by the sensor.

In other words, the measured variable detected by the sensor, which reflects the disinfection intensity actually effected by the disinfection device, can be used to not only control but also regulate the operation of the disinfection device by suitably setting the operating parameter. The measured variable detected by the sensor can serve here as a control variable in a control loop.

According to one embodiment, it can be particularly preferred here to monitor the operating parameter of the disinfection device, which correlates with a current disinfection intensity to be effected, continuously or at suitable time intervals and, if the operating parameter exceeds a predetermined threshold value, to issue a warning signal indicating an approaching end of a service life of the disinfection device.

In other words, the operating parameter at which the disinfection device is operated and which correlates with the disinfection intensity effected can be monitored and checked to see how this parameter behaves in relation to a predetermined threshold. Initially, the disinfection device is operated with an operating parameter that is significantly below this threshold value. By successively increasing the operating parameter, the latter approaches the threshold value over time. The threshold value can be less than or equal to a maximum permissible value of the operating parameter. If the threshold value is equal to the maximum permissible value of the operating parameter, reaching the threshold value means that the operating parameter should not be increased any further, because otherwise there is a risk of disadvantages, such as damage to the disinfection device. Reaching the threshold value thus corresponds to reaching an end of service life of the disinfection device, so that the disinfection device should be serviced or replaced. Preferably, the threshold value is selected to be slightly lower than the maximum permissible value of the operating parameter. Accordingly, reaching the threshold value then means that although the end of the service life of the disinfection device is imminent, there is preferably still sufficient time for measures, such as maintenance or replacement of the disinfection device.

Upon reaching the threshold value, a corresponding warning signal can be output. This warning signal can be transmitted to the control unit of the passenger transport system, for example. There, the warning signal can be output, for example, in a manner perceptible to a technician. Alternatively, the warning signal can be forwarded by the control unit to an external monitoring device and, for example, can trigger there the initiation of suitable maintenance or replacement measures.

According to one embodiment, the disinfection device further comprises a sensor for detecting a temperature inside the disinfection device and/or for detecting a temperature in an environment adjacent to the disinfection device. Here, the control unit of the passenger transport system and/or the controller of the disinfection device are adapted to control the operation of the disinfection device depending on the temperature detected by the sensor.

It has been recognized that some disinfection devices can change the disinfection effects they have created depending on temperature conditions or can even be damaged at certain temperature conditions. For example, it has been recognized that UVC LEDs should not be operated above certain temperature limits because otherwise they will be damaged.

It is therefore proposed to equip the disinfection device with a sensor by means of which the temperature of the disinfection device or individual components thereof and/or an ambient temperature can be determined. A sensor signal representing this temperature can then be taken into account by the controller of the disinfection device and/or the control unit of the passenger transport system when controlling the operation of the disinfection device. For example, in the event of increased measured temperatures, power supply to the disinfection device can be reduced or limited in order to counteract further heating.

With regard to the above-described embodiment of the disinfection device with a sensor for detecting a measured variable correlating with the disinfection intensity and/or with a temperature sensor, according to one embodiment, the controller of the disinfection device can be adapted to send the measured variable determined by the sensor and/or a data signal correlating with the measured variable determined by the sensor to the control unit of the passenger transport system.

In other words, the controller of the disinfection system can preferably not only transmit status signals concerning the current operation, state or configuration of the disinfection system to the control unit of the passenger transport system, but also make measured variables from sensors integrated in the disinfection system available to the control unit. In doing so, either the measured variable itself determined by the sensor or a data signal determined by processing this measured variable can be sent to the control unit.

The control unit itself can then process the information contained therein, for example, and use it when controlling the disinfection device or other components. Alternatively or additionally, the control unit can store the corresponding data for later use and/or forward it to other components. In particular, the data can be forwarded, for example, to an external computer that is part of a remotely arranged monitoring device or a data cloud ("cloud"). There, the measured variables determined can be monitored and/or processed.

According to one embodiment, the passenger transport system can have an interface device for this purpose, which is adapted to send data from the control unit of the passenger transport system to the remotely arranged computer and/or to provide data from the remotely arranged computer available for reception by the control unit of the passenger transport system.

In other words, the passenger transport system can have the possibility to exchange data or signals with a remotely arranged computer using the interface device. The remotely arranged computer can be located outside of the building in which the passenger transport system is installed. In particular, the remotely arranged computer can be part of an external monitoring device by means of which the passenger transport system or its operation is to be monitored. Alternatively, the computer can be part of a data cloud in which, for example, information concerning the passenger transport system can be stored. The control unit of the passenger transport system can in particular forward signals and data, which it has previously received from the controller of the disinfection system, to the external computer via the interface device.

According to one embodiment of the method for operating the passenger transport system proposed herein, for example, a digital twin of the passenger transport system can be stored in the remotely arranged computer. Properties of the passenger transport system can then be determined based on the digital twin of the passenger transport system, taking into account the status signals transmitted from the controller of the disinfection device.

The wording "digital twin" can stand here for a data set in which physical and/or functional properties of the passenger transport system are reproduced as realistically as possible. For example, the digital twin may contain information about geometric, electrical, magnetic, thermal and/or other properties of the passenger transport system. Based on these data, current or, if necessary, even future properties of the passenger transport system can be calculated, simulated or modeled.

It is now proposed that the status signals which reflect current properties concerning the disinfection facility can be additionally entered into the digital twin. Accordingly, properties of the passenger transport system can be determined even more accurately using the digital twin by also taking into account properties of the disinfection device.

For example, based on information which provide insight into disinfection intensity and/or disinfection activity during a past operating period of the passenger transport system, a conclusion can be drawn on a resulting influence on other components of the passenger transport system.

Specifically, in an example in which the disinfection device generates the disinfection effect by means of UVC LEDs, information about operating times and/or lighting intensities, it is possible, by entering this information into a digital twin, to draw conclusions about, for example, the extent to which UVC radiation emitted in this way could have damaged other components of the passenger transport system over time, such as a fabric and/or a plastic material of a handrail of an escalator.

According to a further embodiment, the disinfection device can further comprise an output device which is adapted to output a signal which can be perceived by a human being and which indicates a current state of the disinfection device.

In other words, an output device, for example, in the form of a light source, a display, a loudspeaker or a similar technical component, by means of which a signal can be output that can be perceived by humans visually, acoustically or in another way, can be provided directly on the disinfection device.

This output device can be used, for example, to provide a maintenance technician with information about the current status of the disinfection device. Thus, the maintenance technician can determine directly on site and in a simple manner whether the disinfection device is functioning as expected or, for example, needs to be serviced or replaced. The output device can also be a screen or an optical display, which is visibly arranged for users of the passenger transport system 1 and indicates to them that the disinfection device works and that they can therefore expect disinfected handrails.

It is noted that some of the possible features and advantages of the disclosure are described herein with reference to various embodiments of a passenger transport system, on the one hand, and a method of operating this transport system, on the other hand. A person skilled in the art will recognize that the features can be combined, adapted or interchanged in a suitable manner in order to arrive at further embodiments of the disclosure.

BRIEF DESCRIPTION OF THE DRAWINGS

Embodiments of the disclosure are described below with reference to the accompanying drawing, wherein neither the drawing nor the description is to be construed as limiting the disclosure.

FIG. 1 shows a simplified view of a passenger transport system designed as an escalator with a handrail disinfection device.

The FIGURE is merely schematic and not to scale. Identical reference signs denote identical or similar features.

DETAILED DESCRIPTION

FIG. 1 shows a simplified view of a passenger transport system 1. The passenger transport system 1 designed as an escalator connects a lower level E1 with an upper level E2 of a building structure 5. The passenger transport system 1 can be entered and left again via access areas 3. A circulating step belt 9, which is deflected in the upper level E2 and in the lower level E1 and thus has an advancing section and a returning section, is arranged in a supporting structure 7. For the sake of clarity, the detailed illustration of the returning section has been omitted, as has a detailed illustration of frames, guide rails, and rail blocks. The passenger transport system 1 has a drive unit 11 to drive the step belt 9. Together, the step belt 9 and the drive unit 11 form a passenger conveying device 13, by means of which passengers can be conveyed in the building structure 5 between the access areas 3. A control unit 15 is used to control the operation of the passenger conveying device 13.

The passenger transport system 1 also has two balustrades 17 extending along each longitudinal side of the step belt 9, wherein only the balustrade 17 arranged in the front in the viewing plane is visible in FIG. 1. A handrail 19 is arranged circumferentially on each balustrade 17, its returning strand being guided in a balustrade base 21. This balustrade base 21 connects the balustrade 17 to the supporting structure 7.

Furthermore, the passenger transport system 1 has at least one disinfection device 23 for each circulating handrail 19. For example, the disinfection device is also installed in the balustrade base 21 of the balustrade 17 and is thus concealed from the users of the passenger transport system 1. An operation of the disinfection device 23 is controlled by a controller 25.

In the example shown, the disinfection device 23 can be equipped with one or more UVC LEDs 27. By means of the UVC light emitted from these UVC LEDs 27, a partial surface of the handrail 19 can be irradiated, wherein the high-energy UVC light can kill germs situated there. The controller 25 can control, among other things, a power supply to the disinfection device 23 or to the UVC LEDs 27 thereof.

The disinfection device 23 may further include one or more sensors 29, 31 by means of which operating conditions and/or environmental conditions can be detected. Alternatively, such sensors can also be provided separately and transmit signals to the disinfection device 23. For example, the disinfection device 23 may have a UVC sensor 29, the measurement signals of which indicate what intensity of radiation of UVC light is actually currently being emitted by the UVC LEDs 27 and is striking the UVC sensor 29. Furthermore, a temperature sensor 31 can be provided, by means of which a current temperature of the disinfection device 23 or of components thereof, in particular of the UVC LEDs 27, and/or a temperature of the environment of the disinfection device 23 can be measured.

The disinfection device 23, or its controller 25, and the control unit 15 of the passenger transport system 1 are interconnected via a bidirectional communication system 33. In FIG. 1, the bidirectional communication system 33 is illustrated as a simple line. However, in a practical implementation, it can also be part of a wired bus system or a wireless data communication device.

The controller 25 of the disinfection device 23 is adapted to transmit status signals reflecting information about the current operation, the current state or the current configuration of the disinfection device 23 to the control unit 15 via the communication system 33. Transmitted signals can indicate, for example, an activity of the disinfection device 23, e.g., whether or for how long the disinfection device 23 is being operated. Alternatively or additionally, transmitted signals can indicate information about conditions currently prevailing in the disinfection device 23, e.g., indicate, for example, what temperature is currently being measured by the temperature sensor 31. As a further alternative or addition, transmitted signals can indicate how components of the disinfection device 23 are currently configured, e.g., for example, at what power level the UVC LED 27 is currently operating.

The status signals transmitted by the disinfection device 23 can be received by the control unit 15 and can be processed there. For example, the control unit 15 can take the received status signals into account when controlling functions of the passenger transport system 1.

In particular, the control unit 15 can also control functions of the disinfection device 23 by transmitting suitable control signals to the controller 25 of the disinfection device 23 via the communication system 33. In doing so, the information contained in the previously received status signals can be taken into account, among other things. Hereby it is made possible that the disinfection device 23 can be controlled, for example, by taking into account temperatures currently prevailing therein and/or by taking into account properties of the disinfection device 23 that change over time, for example, due to wear. Furthermore, the control unit 15 can also take into account information regarding other components of the passenger transport system 1 when controlling the disinfection device 23. For example, the control unit 15 can control the operation of the disinfection device 23 in such a manner that a current passenger volume and/or a current speed at which the passenger conveying device 13 or the handrail 19 is displaced is taken into account.

Advantageously, the disinfection device 23 can be designed such that, at least in its new condition, it can be operated in a manner that provides more than a minimum disinfection intensity that is at least required to reliably disinfect a surface 41 to be disinfected. A disinfection device 23 equipped with UVC LEDs 27 can be designed with respect to the UVC LEDs 27 incorporated therein in such a manner that it would already be sufficient for a minimum disinfection intensity to operate the UVC LEDs 27 with, for example, only 80% of their rated power. The rated power here is the maximum power that may be supplied to the UVC LEDs 27 without risking sudden or excessive damage to them.

A disinfection device 23 designed in such a manner is then preferably operated below its rated power, at least initially. In other words, the disinfection device 23 is operated at a disinfection intensity that is above the minimum disinfection intensity but below the maximally achievable maximum disinfection intensity.

A power supply within the disinfection device 23, that is, for example, a current intensity supplied to the UVC LEDs 27, typically correlates with a currently effected disinfection intensity. Initially, this power supply is preferably set lower than the rated power. In this way, energy consumption as well as any potential wear on the disinfection device 23 and/or on surfaces 41 disinfected therewith can be kept low.

However, since it is known, for example, that with the same power supply, UVC LEDs 27 emit less UVC light over time due to wear, the power supply to the UVC LEDs 27 can be successively increased. For example, the power supply can be successively increased at regular intervals or linearly depending on an operating time since start-up of the disinfection device 23. As soon as the power supply approaches or reaches the rated power, this means that the disinfection device 23 or, more specifically, its UVC LEDs 27 have reached their service life and probably need to be replaced.

Since various influences can lead to the fact that the disinfection intensity actually effected by the disinfection device 23 does not change in a unique manner over time, it can be particularly preferred to monitor the disinfection intensity actually effected, for example by means of the UVC sensor 29. Measurement signals from the UVC sensor 29 can then be taken into account by the control unit 15. For example, in the event that a measured UVC light intensity threatens to drop to less than a level necessary for the minimum disinfection intensity, the disinfection device 23 can be energized with a suitably higher power supply.

In this context, it can be advantageous to monitor the actually effected power supply, e.g., in general terms, the operating parameter that correlates with the current disinfection intensity to be effected, and to compare it, for example, with a predetermined threshold value. Specifically, an electrical current intensity supplied to the UVC LEDs 27 may be compared to a current intensity threshold. The threshold value can be set such that it corresponds to the rated power of the UVC LEDs 27 or is below this rated power by a predetermined amount. If the actual effected power supply approaches the rated power and thereby reaches the threshold, this can cause a warning signal to be output which indicates an approaching end of service life of the disinfection device 23. A technician can then service or replace the disinfection device 23. This enables predictive maintenance, since the warning signal can already be generated sufficiently in advance before a failure of the disinfection device 23 actually occurs, either due to damage to its UVC LEDs 27 because of excessive power input, or because the required minimum disinfection intensity can no longer be effected when supplying the rated power.

In addition to being used directly in the control unit 15 of the passenger transport system 1, the status signals transmitted by the controller 25 of the disinfection device 23 can also be advantageously used elsewhere. For example, with the aid of an interface device 37, the control unit 15 may in any case be designed to forward current operating data of the passenger transport system 1 to a remotely arranged computer 35. This remotely arranged computer 35 can be part of a monitoring device or data cloud used to remotely monitor functionalities of the passenger transport system 1. The status signals from the disinfection device 23 can then also be transmitted to such a remotely arranged computer 35. There, they can be used, for example, to monitor functionalities and/or an operating state of the disinfection device 23.

The remotely arranged computer 35 can further be used to remotely control functionalities and/or operating states of the passenger transport system 1 or, more specifically, of the disinfection device 23 thereof. For this purpose, the remotely arranged computer 35 can transmit suitable control signals to the control unit 15 which, based thereon, can in turn send control signals to the controller 25 of the disinfection device 23.

In a particular embodiment, a data set of a digital twin can be stored or maintained on the remotely arranged computer 35. Here, the digital twin indicates structural, physical, and/or functional properties of the passenger transport system 1 and, in particular, of the components installed therein. In this case, the status signals of the disinfection device 23 can be used to maintain the digital twin. For example, data stored in the digital twin can be updated taking into account the information contained in the status signals about the current operation, current state, or current configuration of the disinfection device 23. In this way, current information regarding the disinfection device 23 can always be contained in the digital twin. Furthermore, by means of the updated digital twin, it is also made possible to analyze, model or simulate an influence caused by the disinfection device 23 on other components or parameters of the passenger transport system 1. For example, it is hereby possible to draw a conclusion on an influence that UVC light emitted by the disinfection device 23 may have on other components such as, in particular, the surface 41 to be disinfected of, for example, the handrail 19.

In order to simplify maintenance of the passenger transport system 1 for a maintenance technician on site, the passenger transport system 1 can further comprise an output device 39 which can output information about the current state of the disinfection device 23 in a manner perceptible to the maintenance technician. For example, an LED emitting in the visible spectrum can be provided for this purpose. Depending on which signal is output by the output device 39, e.g., for example, with which color and/or flashing sequence its LED is operated, this can signal to the maintenance technician that (i) the disinfection device 23 is operating properly (e.g., the LED is permanently lit), (ii) the disinfection device 23 is still operating, but is nearing the end of its service life (e.g., slow flashing of the LED), (iii) the disinfection device 23 has already reached the end of its service life (e.g., fast flashing of the LED), or (iv) the disinfection device 23 is currently switched off (e.g., LED off).

The output device 39 can also be a screen or an optical display, which is visibly arranged for users of the passenger transport system 1 and indicates to them that the disinfection device 23 works and that they can therefore expect disinfected handrails 19.

In summary, by means of the bidirectional signal exchange proposed herein between the controller 25 of the disinfection device 23 and the control unit 15 of the passenger transport system 1, the disinfection device 23 can be operated as required and information relating to the disinfection device 23 can be processed by the control unit 15 of the passenger transport system 1 and can be used, for example, to be able to detect wear of the disinfection device 23 and to plan countermeasures at an early stage. Furthermore, the disinfection device 23 can be controlled from a remotely arranged computer 35 via the connection thereof to the control unit 15, or information concerning the disinfection device 23 can be forwarded to the remotely arranged computer 35 and used there, for example, to maintain a digital twin of the passenger transport system 1.

Finally, it should be noted that terms such as "including", "comprising", etc. do not exclude other elements or steps, and terms such as "a" or "an" do not exclude a plurality. It should further be noted that features or steps that have been described with reference to any of the above exemplary embodiments can also be used in combination with other features or steps of other exemplary embodiments described above. Reference signs in the claims are not to be regarded as a limitation.

The invention claimed is:

1. A disinfection device for disinfecting a surface on a passenger conveying device, wherein the passenger conveying device is part of a passenger transport system and is used for conveying passengers within a building structure, the device comprising:

a controller for controlling an operation of the disinfection device, wherein the controller is configured to be connected to a control unit of the passenger transport system via a bidirectional communication system, and at least one ultraviolet-C light emitting diode, wherein the controller of the disinfection device is configured to send status signals, which reflect information about at least one of a current operation, a current state, or a current configuration of the disinfection device, to the control unit and to receive control signals generated by the control unit of the passenger transport system taking into account received status signals, wherein the controller controls the operation of the disinfection device taking into account received control signals, wherein the controller of the disinfection device is configured to control a disinfection intensity of the at least one ultraviolet-C light emitting diode with which the disinfection device disinfects a surface to be disinfected, depending on control signals which are transmitted to the controller by the control unit of the passenger transport system and which indicate an operating parameter of the disinfection device correlating with a disinfection intensity of the at least one ultraviolet-C light emitting diode currently to be effected, wherein the control unit of the passenger transport system or the controller of the disinfection device are adapted to increase the operating parameter of the disinfection device correlating with a currently effected disinfection intensity of the at least one ultraviolet-C light emitting diode depending on an operating time since start-up of the disinfection device.

2. A passenger transport system, comprising:

a passenger conveying device for conveying passengers within a building structure;

a control unit for controlling an operation of the passenger conveying device; and a disinfection device for disinfecting a surface to be disinfected on the passenger conveying device;

wherein the disinfection device comprises a controller for controlling an operation of the disinfection device and at least one ultraviolet-C light emitting diode;

wherein the controller of the disinfection device is connected to the control unit of the passenger transport system via a bidirectional communication system, and wherein the control unit of the passenger transport system and the controller of the disinfection device are adapted in such a manner that status signals, which reflect information about a current operation, a current state and/or a current configuration of the disinfection device, are sent from the controller to the control unit, and the control unit generates control signals taking into account received status signals and transmits them to the controller, wherein the controller controls the operation of the disinfection device taking into account received control signals, wherein the controller of the disinfection device is adapted to control a disinfection intensity of the at least one ultraviolet-C light emitting diode with which the disinfection device disinfects the surface to be disinfected depending on control signals which are sent to the controller by the control unit of the passenger transport system and which indicate an operating parameter of the disinfection device correlating with a disinfection intensity of the at least one ultraviolet-C light emitting diode currently to be effected, wherein the control unit of the passenger transport system or the controller of the disinfection device are adapted to increase the operating parameter of the disinfection device correlating with a currently effected disinfection intensity of the at least one ultraviolet-C light emitting diode depending on an operating time since start-up of the disinfection device.

3. The system of claim 2, wherein the control unit generates control signals which indicate a setpoint value for the operating parameter of the disinfection device correlating with a disinfection intensity of the at least one ultraviolet-C light emitting diode currently to be effected, taking into account the status signals received from the controller.

4. The system of claim 2, wherein:
the disinfection device is configured to be able, in a new state, to effect as a maximum disinfection intensity of the at least one ultraviolet-C light emitting diode a disinfection intensity of the at least one ultraviolet-C light emitting diode which is greater than a minimum disinfection intensity necessary for sufficient disinfection of the surface to be disinfected, and
the control unit of the passenger transport system or the controller of the disinfection device are adapted to operate the disinfection device in normal operation with a disinfection intensity of the at least one ultraviolet-C light emitting diode above the minimum disinfection intensity and to successively increase an operating parameter of the disinfection device correlating with a currently effected disinfection intensity of the at least one ultraviolet-C light emitting diode.

5. The system of claim 2, wherein:
the disinfection device further comprises a sensor for detecting a measured variable which correlates with the disinfection intensity of the at least one ultraviolet-C light emitting diode, and
the control unit of the passenger transport system and/or the controller of the disinfection device are adapted to increase the operating parameter of the disinfection device correlating with a currently effected disinfection intensity of the at least one ultraviolet-C light emitting diode depending on the measured variable detected by the sensor.

6. The system of claim 5, wherein the control unit of the passenger transport system or the controller of the disinfection device are adapted to regulate the operating parameter of the disinfection device correlating with a currently effected disinfection intensity of the at least one ultraviolet-C light emitting diode depending on the measured variable detected by a sensor.

7. The system of claim 2, wherein the operating parameter of the disinfection device correlating with a disinfection intensity of the at least one ultraviolet-C light emitting diode currently to be effected is monitored and, if the operating parameter exceeds a predetermined threshold value, a warning signal is output which indicates an approaching end of a service life of the disinfection device.

8. The system of claim 2, wherein:
the disinfection device further comprises a sensor for detecting a temperature inside the disinfection device or for detecting a temperature in an environment adjacent to the disinfection device, and
the control unit of the passenger transport system or the controller of the disinfection device are adapted to control the operation of the disinfection device depending on the temperature detected by the sensor.

9. The system of claim 5, wherein the controller of the disinfection device is adapted to send the measured variable determined by the sensor or a data signal correlating with the measured variable determined by the sensor to the control unit of the passenger transport system.

10. The system of claim 2, wherein the passenger transport system further comprises an interface device adapted to send data from the control unit of the passenger transport system to a remotely arranged computer and/or to provide data from a remotely arranged computer for reception by the control unit of the passenger transport system.

11. The system of claim 2, wherein the control unit generates the control signals taking into account information about a speed at which the passenger conveying device is operated and/or a number of passengers conveyed by the passenger conveying device.

12. The system of claim 2, wherein the disinfection device further comprises an output device, which is adapted to output a signal which can be perceived by a human being and which indicates a current state of the disinfection device.

13. A method for operating a passenger transport system, the passenger transport system comprising a passenger conveying device for conveying passengers within a building structure, a control unit for controlling an operation of the passenger conveying device, and a disinfection device for disinfecting a surface to be disinfected on the passenger conveying device, wherein the disinfection device comprises a controller for controlling an operation of the disinfection device and at least one ultraviolet-C light emitting diode, and wherein the controller of the disinfection device is connected to the control unit of the passenger transport system via a bidirectional communication system, the method comprising:
transmitting status signals reflecting information about at least one of a current operation, a current state, or a current configuration of the disinfection device from the controller to the control unit, and
controlling an operation of the disinfection device taking into account received control signals which are transmitted from the control unit to the controller taking into account received status signals,
controlling the operation of the disinfection device by increasing an operating parameter of the disinfection device correlating with a currently effected disinfection intensity of the at least one ultraviolet-C light emitting diode depending on an operating time since start-up of the disinfection device,
wherein the status signals are sent from the control unit to a remotely arranged computer and processed there or wherein control signals are transmitted from the remotely arranged computer to the control unit and from the control unit further to the controller to control the operation of the disinfection device.

14. The method according to claim 13, wherein a digital twin of the passenger transport system is stored in the remotely arranged computer and wherein properties of the passenger transport system are determined based on the digital twin of the passenger transport system taking into account the status signals transmitted by the controller of the disinfection device.

* * * * *